(12) United States Patent
Golz-Berner et al.

(10) Patent No.: US 7,731,942 B2
(45) Date of Patent: Jun. 8, 2010

(54) COSMETIC TREATMENT FOR BODY-MODELLING WITH SUN PROTECTION AND MODELLING KIT

(75) Inventors: Karin Golz-Berner, Monaco (MC); Leonhard Zastrow, Monaco (MC)

(73) Assignee: Coty Prestige Lancaster Group GmbH, Mainz (DE)

( * ) Notice: Subject to any disclaimer, the term of this patent is extended or adjusted under 35 U.S.C. 154(b) by 86 days.

(21) Appl. No.: 11/912,638

(22) PCT Filed: May 4, 2006

(86) PCT No.: PCT/EP2006/062039

§ 371 (c)(1),
(2), (4) Date: Oct. 25, 2007

(87) PCT Pub. No.: WO2006/117392

PCT Pub. Date: Nov. 9, 2006

(65) Prior Publication Data

US 2008/0226570 A1    Sep. 18, 2008

(30) Foreign Application Priority Data

May 4, 2005    (DE) .................. 10 2005 021 805

(51) Int. Cl.
*A61K 8/18*    (2006.01)
*A61K 8/02*    (2006.01)

(52) U.S. Cl. ........................ 424/59; 424/401

(58) Field of Classification Search .................. 424/59, 424/401
See application file for complete search history.

(56) References Cited

U.S. PATENT DOCUMENTS

| 4,288,433 A | 9/1981 | Koulbanis et al. | |
|---|---|---|---|
| 4,419,343 A | 12/1983 | Pauly et al. | |
| 4,793,990 A * | 12/1988 | Grollier et al. | 424/59 |
| 6,001,366 A | 12/1999 | Vacher et al. | |
| 6,245,342 B1 * | 6/2001 | Golz-Berner et al. | 424/401 |
| 6,270,781 B1 * | 8/2001 | Gehlsen | 424/401 |
| 6,426,080 B1 * | 7/2002 | Golz-Berner et al. | 424/401 |
| 6,960,354 B1 * | 11/2005 | Leigh et al. | 424/450 |
| 2002/0131948 A1 * | 9/2002 | Toumi et al. | 424/70.12 |
| 2003/0170333 A1 * | 9/2003 | Golz-Berner et al. | 424/777 |
| 2004/0180069 A1 * | 9/2004 | Bleuez et al. | 424/401 |
| 2004/0191330 A1 * | 9/2004 | Keefe et al. | 424/638 |
| 2005/0025737 A1 | 2/2005 | Sebagh | |
| 2009/0041685 A1 * | 2/2009 | Baviskar et al. | 424/59 |

FOREIGN PATENT DOCUMENTS

| WO | WO 99/66881 | 12/1999 |
|---|---|---|
| WO | WO 2004/002435 | 1/2004 |
| WO | WO 2004/103334 | 12/2004 |

OTHER PUBLICATIONS

Alvarez et al., "Lipids in pharmaceutical and cosmetic preparations," Grasys Y Aceites, 51(1-2), pp. 74-96, 2000.
Briand, "Algal Active Substances," Cosmetics & Toiletries, vol. 118, No. 2, Feb. 2, 2003.
Gottschalk et al., International Cosmetic Ingredient Dictionary and Handbook, The Cosmetic, Toiletry & Fragrance Assoc., Washington, DC, 10th ed., p. 3323, 2004.
Sun screens & UV protection, 2004, available at http//www.ispcorp.com/innews/technical/cosmscience/04.

* cited by examiner

*Primary Examiner*—Johann R Richter
*Assistant Examiner*—Luke E Karpinski
(74) *Attorney, Agent, or Firm*—Novak Druce + Quigg; Gregory A. Nelson; Gregory M. Lefkowitz

(57) ABSTRACT

The invention relates to a method for body shaping by means of a sun-protection agent and a corresponding cosmetic product. The inventive method consists in pre-treating by means of a preliminary product containing a caffeine, algae extract, pineapple extract, radical scavenger, copper gluconate, silyl-propionic acid and a melanin-stimulating amino acid-containing agent, in subsequently treating by a main product containing, apart from an UVA- and UVB-Filter, at an ratio ranging from 30:70 to 70:30, a green coffee bean oil whose radical scavenger content is 30-60% less than this of the preliminary agent and in post-treating by means of an after-product which comprises the preliminary product constituents and whose silylpropionic acid content is of 2 to 10 times the content of the preliminary product.

13 Claims, No Drawings

COSMETIC TREATMENT FOR BODY-MODELLING WITH SUN PROTECTION AND MODELLING KIT

The invention relates to a method for body modelling, which method involves a sunscreen and a cosmetic product consisting of single components.

The use of various substances in cosmetic slimming products is known from WO 2004/103334. These include cafestol or kahweol as extracts of green coffee beans, while the use of caffeine tends to be regarded as disadvantageous. The use of peptides having the sequence Ser-Val-Ser-Glu-Ile-Gln-Leu-Met-His-Asn (WO 00/04047) or of particular plant extracts is also well-known.

The invention is based on the object of developing a cosmetic method providing simultaneous UV protection, body modelling and sustaining skin tan under intense sun exposure.

According to the invention, the cosmetic method of body modelling with the use of sunscreen is constituted of the following:

a) 2-4 weeks prior to expected intense sun irradiation on the skin, a pre-product is applied to selected areas of the skin once to twice a day, said pre-product comprising
   0.5-3 wt.-% caffeine, preferably 1 to 2.5%, 0.1-2.5 wt.-% of an algae extract of *Gelidium* s.p., preferably 0.5 to 2.0%,
   0.05-2 wt.-% of a pineapple fruit extract, preferably 1 to 1.5 wt.-%,
   0.3-2.5 wt.-% of a radical scavenger, preferably 0.5 to 2 wt.-%,
   0.005-0.1 wt.-% of copper gluconate,
   0.05-0.5 wt.-% of a silylpropionic acid, and
   0.1-1 wt.-% of a stimulant for melanin synthesis, comprising sorbitol and Arg-HCl, Orn-HCl and Tyr,
   wherein all wt.-% are based on the overall weight of the preproduct, with the proviso that the quoted amounts are balanced with water and optionally further adjuvants and additives to make 100 wt.-%;

b) during intense sun irradiation, a main product is applied to the skin, comprising the components of the preproduct and, in addition, a mixture of UVA and UVB filters at a weight ratio of 30:70 to 70:30 and in a share of 5 to 40 wt.-%, and
   0.01-3.0 wt.-% of an encapsulated oil of green coffee beans, relative to the overall weight of the main product, the share of radical scavenger being 30-60% lower than that in the preproduct, relative to the weight of radical scavenger in the preproduct, with the proviso that the quoted amounts are balanced with water and optionally further adjuvants and additives to make 100 wt.-%; and c) after intense sun irradiation, a secondary product is applied to the skin, comprising the components of the preproduct, the share of silylpropionic acid being 2 to 10 times the share in the preproduct, ranging from 0.5 to 2.5 wt.-%, relative to the overall weight of the secondary product, with the proviso that the quoted amounts are balanced with water and optionally further adjuvants and additives to make 100 wt.-%.

In total, the method according to the invention provides high UV protection with sustaining tan extension and, simultaneously, smooth skin and degradation of cutaneous fat reserves.

Advantageously, the weight ratio of UVA and UVB filters ranges from 40:60 to 60:40. The preferred range is from 8 to 28 wt.-%. Also preferred are oil-soluble filters, and the share of physical filters can be up to 20 wt.-%. A person skilled in the art can select a filter depending on the intended sun protection factor (SPF).

Intense sun irradiation is understood to be a quantity of radiation attained either by exposing the skin to direct natural sun radiation on a bright sandy beach for more than 30 minutes, preferably more than 60 minutes, or by using artificial irradiation by means of a sun simulator (XBO 450 W/20FR xenon lamp) with $E_{UVA}$=8.4 mW/cm$^2$ and $E_{UVB}$=0.18 mW/cm$^2$ for more than 20 minutes, this procedure being continued on at least 3 to 6 days.

In a preferred embodiment of the invention, a preproduct is employed including as additive one or more substances selected from the group consisting of
0.5-2 wt.-% cactus blossoms,
0.3-0.8 wt.-% extract of leaves of *Ilex paraguariensis*,
0.05-0.9 wt.-% melanin-activating peptide,
0.8-3.5 wt.-% of a hydrolyzed soy proteins,
0.1-2.5 wt.-% of a plant extract mixture with a diuretic effect.

The algae extract of *Gelidium* s.p., especially *Gelidium cartilagineum*, shows marked lipolytic effectiveness and is able to stimulate the fibroblasts in their lipolytic effect and break up and reduce deposited cell fat reserves. The extract is obtained in propylene glycol at 20-40° C.

The pineapple extract is obtained from fruit pulp using a monohydric alcohol such as ethanol, propanol, isopropanol, butanol, preferably ethanol. Owing to the content of the bromelin enzyme and in combination with the effect of the algae extract, the keratinolytic activity is enhanced, apart from the radical-scavenging activity of vitamin C included therein.

The mixture of sorbitol and amino acid or salts thereof stimulates the melano-genesis, especially of B16 melanocytes. In this way, the skin is better prepared for imminent sun irradiation and tan extension is achieved to a certain degree. A preferred product is Phototan® LS 2261E. Surprisingly, addition of the amino acid glycine with 0.01-0.5 wt.-%, relative to the overall weight of the preproduct of the invention, can contribute to further tan extension.

Vitamins such as vitamin C and derivatives thereof, e.g. ascorbyl acetate, phosphate and palmitate, magnesium ascorbyl phosphate; vitamin A and derivatives thereof; folic acid and derivatives thereof, vitamin E and derivatives thereof, such as tocopheryl acetate; flavones or flavonoids; amino acids such as histidine, glycine, tyrosine, tryptophan and derivatives thereof; carotenoids and carotenes such as α-carotene, β-carotene; lycopin; uric acid and derivatives thereof; α-hydroxy acids such as citric acid, lactic acid, malic acid can be used as radical scavengers.

A well-known effective radical scavenger is an active substance with a high radical protection factor, such as described in WO 99/66881, e.g. the active substance complex in accordance with Example 1 or 2.

Particularly preferred as radical scavenger is a mixture of alcohol-based plant extracts free of liposomes, consisting of 0.1 to 2 wt.-% of an extract of green coffee beans, 0.1 to 2 wt.-% of an extract of *Camellia sinensis* leaves, 0.1 to 2 wt.-% of an extract of Pongamia pinnata, and 0.1 to 2 wt.-% of an extract of *Angelica archangelica* roots and a balance of a monohydric $C_2$-$C_5$ alcohol to make 100 wt.-%, the radical protection factor ranging from 1,400 to 2,900×10$^{14}$ radicals per mg according to WO 2004/105704.

For example, melanin-activating peptides are those having the formula Lip-X-His-Phe-Arg-Y wherein Lip is thioctic acid or a derivative thereof, X is Glu, OH or NH$_2$, Y is Trp-Gly-OH, Trp-Gly-NH$_2$, Trp-OH or Trp-NH$_2$, and Phe is homo-Phe or P-fluoro-Phe (e.g. according to EP 949 902 B1), or the peptide M.A.P.® from Vincience, Sophia-Antipolis, FR.

The oil of green coffee beans is preferably encapsulated in liposomes, using an amount of 0.05 to 0.5 wt.-%, relative to the overall weight of the main product.

Among the group of preferred substances which can be added to the preproduct as additive, the plant extract mixture having a diuretic effect and the *Ilex paraguariensis* extract are particularly preferred. The aqueous plant extract mixture is constituted of *Lepedeza capitata, Ulva lactuca, Glycyrrhiza glabra, Combretum micanthum*. Inter alia, flavonoid tannins and polyphenols are supplied with the above mixture, and apart from the diuretic effect, a tonic effect and elimination of metabolic residual substances is achieved. A preferred product is Sveltonyle® LS 8989, in which case the active substance content ranges from 0.02 to 0.05%, relative to the dry weight of the product.

The *Ilex paraguariensis* extract is an extract of leaves obtained using higher alcohols, e.g. propylene glycol, butylene glycol, glycerol, and contributes to a reduction of volume and number of adipocytes and a reduction of lipid accumulations. A preferred product is Unislim® from Sederma, FR.

The hydrolyzed soy protein promotes contraction of the collagen fibers and protects the elastin fibers from enzymatic attack.

Preferably, the silylpropionic acid is a methylsilanetriol, specifically 2-[(dihydroxy-methylsilyl)oxy]propionic acid which inhibits the glycosylation reaction (glycation) of proteins and sugars in the form of Maillard's reaction which is known to cause skin ageing as a result of loss of elasticity. Surprisingly, said inhibiting effect is enhanced by a cactus blossom extract which, in addition, exhibits very good hemostatic, draining and anti-edema effects. Preferred is an aqueous extract of blossoms of *Opuntia coccinellifera*.

Optional addition of 0.1-1.5 wt.-% of a caper extract in the secondary product of the invention achieves an improvement in the susceptibility to inflammatory reactions in sensitive skin. Particularly preferred is an extract of *Capparis spinosa* with octyldodecyl myristate and supercritical $CO_2$.

Advantageously, the secondary product may also include a hydrolyzed *Citrus aurantinum* extract which contains about 4-8 wt.-% of pure fruit extract in addition to water. The share of extract can be 0.5-2 wt.-%, relative to the overall weight of secondary product. Surprisingly, together with the other active components, this achieves a more intense tanning effect over a prolonged period of time.

UV filters employed in the main product are preferably 4-aminobenzoic acid derivatives such as 2-ethylhexyl 4-dimethylaminobenzoate; esters of cinnamic acid such as 2-ethylhexyl 4-methoxycinnamate; 3-benzylidenecamphor derivatives such as 3-benzylidenecamphor, octyl methoxycinnamate, isoamyl p-methoxycinnamate, ethylhexyl methoxycinnamate, octyl salicylate, 4-methylbenzylidenecamphor, homosalates and octyl dimethyl PABA, or salicylic acid derivatives such as ethylhexyl salicylate or homomenthyl salicylate.

Preferred UVA filters are butylmethoxybenzoylmethane, 1-phenyl-4-(4'-isopropyl-phenyl)propane-1,3-dione, menthyl anthranilate and bis-ethylhexyloxyphenol/methoxyphenyltriazine.

Physical filters are understood to be inorganic filters such as titanium dioxide, zirconium oxide, zinc oxide, silicon dioxide etc.

Furthermore, components of the above-mentioned preproduct, main product and secondary product can be cosmetic adjuvants, excipients and additives as usually employed in such preparations, e.g. water, preservatives, dyes, pigments with a coloring effect, thickeners, fragrances, alcohols, polyols, esters, electrolytes, gelling agents, polar and non-polar oils, polymers, copolymers, emulsifiers, waxes and stabilizers.

The oils used in the invention can be conventional cosmetic oils such as mineral oil, hydrogenated polyisobutene, squalane produced synthetically or from natural products, cosmetic esters or ethers which can be branched or unbranched, saturated or unsaturated; vegetable oils; or mixtures of two or more thereof.

Especially suitable oils are, for example, silicone oils, as well as vegetable oils such as calendula oil, jojoba oil, avocado oil, macadamia nut oil, castor oil, cocoa butter, coconut oil, maize oil etc.

The preproduct, main product and secondary product according to the invention can also be formulated with gelling agents. Suitable gelling agents include carbomer, xanthan gum, carrageenan, acacia gum, guar gum, agar, alginates and tyloses, carboxymethylcellulose, hydroxyethylcellulose, quaternized cellulose, quaternized guar, specific polyacrylates, polyvinyl alcohol, polyvinylpyrrolidone, montmorillonite. Preferred is carbomer.

Furthermore, pigments, pigment mixtures or powders having a pigment-like effect, also including those having a nacreous effect, can be added, comprising e.g. iron oxides, natural aluminum silicates such as ocher, titanium dioxide, mica, kaolin, manganese-containing clays, calcium carbonate, talc, mica-titanium oxide, mica-titanium oxide-iron oxide, bismuth oxychloride, nylon beads, ceramic beads, expanded and non-expanded synthetic polymer powders, powdered natural organic compounds such as ground solid algae, ground plant parts, encapsulated and non-encapsulated grain starches.

Likewise, polyols are possible components of the sun product according to the invention. For example, polyols are propylene glycol, dipropylene glycol, ethylene glycol, isoprene glycol, glycerol, butylene glycol, sorbitol and mixtures thereof. The share of polyol is in the range of from 2 to 10 wt.-%, preferably from about 2 to about 7 wt.-%, relative to the overall weight of the product.

In the method according to the invention the skin is preferably subjected to a cleansing treatment with a skin peel prior to applying the preproduct. This can be a conventional skin cleanser that is able to remove skin scales and dead cells and open the pores. For example, such a skin peel can be a gel including e.g. 0.5 to 3 wt.-% of a grainy powder of NaCl, sugar and optionally polyethylene.

All components in the preproduct, main product and secondary product of the method according to the invention are well-balanced. Intensive skin smoothing is seen in all phases of the treatment, i.e., the appearance of the skin is significantly improved. In addition, accumulations of fat in the skin are reduced.

In contrast to well-known spa wellness products, no additional measures of massage are required, and no specific instructions of use must be observed, except for the order of product application. The method is particularly suitable for easy integration in the course of a vacation where physical exercise is involved in product application, lastingly supporting the modelling effect.

Compared to conventional pre-sun/sun/after-sun products, a significant improvement in skin smoothness is achieved in consumer tests (no orange-peel skin on thighs in about 90%); skin fat pads are reduced.

In particular, an essentially constant skin tan after finishing the treatment with secondary product is seen for about another 4 weeks, being about 80% of the original tan.

The invention is also directed to a set for cosmetic body modelling with the use of sunscreen, characterized in that the set comprises a preproduct comprising 0.5-3 wt.-% caffeine, 0.1-2.5 wt.-% of an algae extract of *Gelidium* s.p., 0.05-2 wt.-% of an encapsulated pineapple fruit extract, 0.3-2.5 wt.-% of a radical scavenger, 0.005-0.1 wt.-% copper gluconate, 0.05-0.5 wt.-% of a silylpropionic acid, and 0.1-1 wt.-% of a stimulant for melanin synthesis, comprising sorbitol and Arg-HCl, Orn-HCl and Tyr, wherein all wt.-% are based on the overall weight of the preproduct, with the proviso that the quoted amounts are balanced with water and optionally further adjuvants and additives to make 100 wt.-%;

a main product comprising the components of the preproduct and, in addition, a mixture of UVA and UVB filters at a weight ratio of 30:70 to 70:30 and in a share of 5 to 40 wt.-%, and 0.01-3.0 wt.-% of an encapsulated oil of green coffee beans, relative to the overall weight of the main product, the share of radical scavenger being 30-60% lower than that in the preproduct, relative to the weight of radical scavenger in the preproduct, with the proviso that the quoted amounts are balanced with water and optionally further adjuvants and additives to make 100 wt.-%;

a secondary product comprising the components of the preproduct, the share of silylpropionic acid being 2 to 10 times the share in the preproduct, ranging from 0.5 to 2.5 wt.-%, relative to the overall weight of the secondary product, with the proviso that the quoted amounts are balanced with water and optionally further adjuvants and additives to make 100 wt.-%.

In one particular embodiment the set can be supplemented by a skin cleansing agent (peel).

The invention will be explained in greater detail below with reference to examples. All the details are given in weight percent unless otherwise stated.

EXAMPLE 1

(A) Skin Peel

Phase A
Water q.s. ad 100; carbomer 2.0; glycerol 5.0.

Phase B
Triethanolamine 2.0

Phase C
Ethanol 2.0; peeling grains 2.0; perfume 0.8; preservative 0.9.

The components of the phases are mixed one after the other, and the phases are mixed together in the order specified above.

(B) Preproduct (Pre-Sun)

Phase A
Water q.s. ad 100; caffeine 2.8; propylene glycol 2.0; xanthan gum 0.5; acrylates/vinyl isododecanoate crosspolymer 0.5.

Phase B
Cyclopentasiloxane, cyclohexasiloxane, cyclotetrasiloxane 3.0; silicone 5.0.

Phase C
Algae extract of *Gelidium cartilagineum* 0.8; pineapple extract 1.0; RPF complex[1] 1.0; copper gluconate 0.01; silylpropionic acid 0.08; hydrolyzed Citrus aurantinum extract 0.1; perfume 0.8; preservative 0.9.

[1] According to Example 1 WO 99/66881.

The single components of the phases are mixed separately. Thereafter, phases A and B are mixed together at 70° C., stirred and cooled to 38° C. at maximum. Phase C is subsequently added with stirring, and the mixture is homogenized.

(C) Main Product (Sun Modelling SPF 15)

Phase A
Water q.s. ad 100; caffeine 2.8; glycerol 3.0; xanthan gum 0.4.

Phase B
Tribehenin PEG-20 ester 1.0; stearic acid 1.2; PEG-100 stearate 2.5; glyceryl stearate 2.5; 4-methylbenzylidenecamphor 3.0; bis-ethylhexyloxyphenone-meth-oxyphenyltriazine 1.0; butylmethoxydibenzoylmethane 3.0; ethylhexyl methoxy-cinnamate 7.5; ethylhexyl salicylate 5.0; cyclopentasiloxane, cyclohexasiloxane, cyclotetrasiloxane 4.0; $C_{12}$-$C_{15}$-alkyl benzoate 2.5.

Phase C
Algae extract of *Gelidium cartilagineum* 0.5; pineapple extract 0.5; RPF complex[1] 0.5; copper gluconate 0.01; silylpropionic acid 0.05; hydrolyzed *Citrus aurantinum* extract 0.5; green caffeine oil liposomes 0.5; perfume 0.8; preservative 1.0.

The single components of the phases are mixed separately at 75° C. Subsequently, phases A and B are stirred together homogeneously at 75° C. and cooled to about 40° C. with stirring. Thereafter, phase C is added with stirring, and the mixture is homogenized.

(D) Secondary Product (After-Sun)

Phase A
Water q.s. ad 100; caffeine 0.8; glycerol 8.5.

Phase B
Beheneth-25 3.5; cetearyl alcohol 3.0; dicapryl carbonate 8.0; Shea butter 7.0;

Phase C
Algae extract of *Gelidium cartilagineum* 2.1; pineapple extract 1.0; RPF complex[1] 1.0; copper gluconate 0.01; silylpropionic acid 0.08; hydrolyzed *Citrus aurantinum* extract 0.1; panthenol 1.0; perfume 0.8; preservative 0.9.

The procedure corresponds to that of part (B).

EXAMPLE 2

The composition corresponds to that of Example 1, with the following modifications:

The preproduct additionally includes 0.5% cactus blossoms and 0.1% *Ilex paraguariensis*.

EXAMPLE 3

The composition corresponds to that of Example 1, with the following modifications:

The preproduct additionally includes 0.5% cactus blossom extract; 0.1 flex para-guariensis; 0.1% melanin-activating peptide MAP® X; 1.0% hydrolyzed soy protein; 1.5% plant extract mixture Sveltonyl LS® 8989 with diuretic effect.

EXAMPLE 4

The composition corresponds to that of Example 3, with the following modifications:

Preproduct and secondary product each include 1.9% algae extract of *Gelidium cartilagineum* and 0.4% pineapple extract; the main product includes 0.8% Green Caffeine Oil Liposomes.

EXAMPLE 5

The composition corresponds to that of Example 2, with the following modifications:
The preproduct includes 0.3% silylpropionic acid, and the secondary product includes 0.85% silylpropionic acid. As radical scavenger, the preproduct includes tocopherol in liposomes and tocopheryl acetate (1.3%); the main product includes tocopherol in liposomes and tocopheryl acetate (0.8%) as radical scavenger.

EXAMPLE 5

Comparative Example

For comparison, a standard commercial combined cosmetic preparation was used, consisting of a pre-sun product, a sun product and an after-sun product.
Pre-sun: Phase A: water q.s. ad 100; glycerol 5.0. Phase B: ethylhexyl methoxycinnamate 3.0; sodium phenylbenzimidazole sulfonate 2.5; ethylhexyltriazone 1.5; butyl-methoxydibenzoylmethane 2.0. Phase C: ethanol 2.0; panthenol 1.0; tocopheryl acetate 0.5; allantoin 0.5; perfume 0.5; preservative 0.5.
Sun SPF 15: Water q.s. ad 100; glycerol 2.5; carbomer 1.2; propylene glycol 0.5. Phase B: isoamyl p-methoxycinnamate 7.5; ethylhexyl salicylate 5.0; dicaprylyl carbonate 5.0. Phase C: tocopheryl acetate 0.5; panthenol 0.5; perfume 0.98; preservative 0.7. Phase D: triethanolamine 1.3.
After-sun: Phase A: water q.s. ad 100; glycerol 8.0; ethanol 2.0. Phase B: cetearyl isononanoate 3.2; VP/hexadecene copolymer 0.8; acrylates/$C_{10}$-$C_{30}$ alkyl acrylate copolymer 2.5; tocopheryl acetate 0.3; allantoin 1.0; bisabolol 1.0; Aloe barbadensis 0.5; perfume oil 0.5; preservatives 0.5.

A user test was performed on 20 female subjects 35 to 52 years of age. In test phase 1 the subjects received the three above-mentioned commercially available products in the form of pre-sun product, sun product with SPF 15 and after-sun product. The products were applied once a day over a period of 14 days each time. This was followed by an interruption of four weeks. In the subsequent test phase 2 the subjects received creams/lotions in accordance with Example 1 of the invention, including the peel beforehand. The products of the invention were invariably rated better by the subjects. Specifically, the following positive opinions on the product combination of the invention were recorded (average values in %):

| | |
|---|---|
| Soothing irritations | 88 |
| Reducing redness | 94 |
| Reducing sunburn | 88 |
| Skin-soothing | 96 |
| Smooth skin | 92 |
| Regenerated skin | 93 |
| Long-lasting tan | 91 |
| Even tan | 89 |

After test phase 2, the thigh circumference of the subjects was reduced by 1.8 to 2.4 cm on an average.
After test phase 1 and prior to beginning test phase 2, the skin tan of the subjects (group A) was determined by the test personnel in a particular area of the skin, using a shades of brown color chart from 1 to 10 (10=darkest brown). A second group (group B) received only the preparations in accordance with Example 1. 4 weeks after completing the test phase, this group was likewise subjected to a color comparison.

| | |
|---|---|
| Group A average value after test phase 1: | 8.3 |
| Group A average value after test phase 1 + 4 weeks: | 6.6 |
| Group B average value after test phase: | 8.7 |
| Group B average value after test phase + 4 weeks: | 8.2 |

The long-lasting tanning effect in group B resulting from the method according to the invention is clearly seen from the above.

EXAMPLE 6

In Vitro Skin Tanning

In vitro tests were performed on normal human melanocytes. Following UVB irradiation, the amount of melanin in the SPF 15 stage was increased by +38% in treated melanocytes compared to untreated melanocytes.

EXAMPLE 7

UV Protection

Cell investigations on the influence of protection of the filter combination in SPF 15 showed the following result:

| | |
|---|---|
| % UVA stopped | 84 |
| % UVB stopped | 94 |
| % UVA + B stopped | 92 |

We claim:
1. A method of body modelling with the use of sunscreen, comprising:
   a) 2-4 weeks prior to expected intense sun irradiation on the skin, a preproduct is applied to selected areas of the skin once to twice a day, active ingredients in said preproduct comprising
      0.5-3 wt.-% caffeine,
      0.1-2.5 wt.-% of an algae extract of *Gelidium* s.p. obtained in propylene glycol,
      0.05-2 wt.-% of a pineapple fruit extract,
      0.3-2.5 wt.-% of a radical scavenger,
      0.005-0.1 wt.-% copper gluconate,
      0.05-0.5 wt.-% of a silylpropionic acid, and
      0.1-1 wt.-% of a stimulant for melanin synthesis, comprising sorbitol and Arg-HCl, Orn-HCl and Tyr,
      wherein all wt.-% are based on the overall weight of the preproduct, with the proviso that the quoted amounts are balanced with water and optionally further adjuvants and additives to make 100 wt.-%;
   b) during intense sun irradiation, a main product is applied to the skin, comprising the active ingredients in the amounts, except for the radical scavenger, of the preproduct and further comprising 5 to 40 wt.-% of a mixture of UVA and UVB filters at a weight ratio of 30:70 to 70:30, and
      0.01-3.0 wt.-% of an encapsulated green coffee bean oil, relative to the overall weight of the main product, the share of radical scavenger being 30-60% lower than that in the preproduct, relative to the weight of radical scavenger in the preproduct, with the proviso that the quoted amounts are balanced with water and optionally further adjuvants and additives to make 100 wt.-%; and c) after intense sun irradiation, a secondary product is applied to the skin, comprising the active ingredients in the amounts, except the silylpropionic acid, of the preproduct, wherein the share of silylpropionic acid is 2 to 10 times the share in the preproduct, said share of silylpropionic acid ranging from 0.5 to 2.5 wt.-%, relative to the overall weight of the secondary product, with the proviso that the quoted amounts are balanced with water and optionally further adjuvants and additives to make 100 wt.-%.

2. The method according to claim 1, wherein a preproduct is employed, including as additive a substance selected from the group consisting of:
0.5-2 wt.-% cactus blossom extract,
0.3-0.8 wt.-% extract of leaves of *Ilex paraguariensis*,
0.05-0.9 wt.-% melanin-activating peptide,
0.8-3.5 wt.-% of a hydrolyzed soy protein,
0.1-2.5 wt.-% of a plant extract mixture with a diuretic effect,
0.01-0.5 wt.-% of the amino acid glycine, and mixtures thereof.

3. The method according to claim 1, wherein the UVA and UVB filters are employed at a weight ratio of from 40:60 to 60:40.

4. The method according to claim 1, wherein oil-soluble UVA and UVB filters are employed.

5. The method according to claim 4, wherein up to 20 wt.-% of the oil-soluble UVA or UVB filter or mixture thereof is replaced by physical filters.

6. The method according to claim 1, wherein an active substance is employed as radical scavenger, which comprises a content of a product obtained by extraction of the bark of *Quebracho Blanco* and subsequent enzymatic hydrolysis, which product includes at least 90 wt.-% proanthocyanidin oligomers and at most 10 wt.-% gallic acid, in microcapsules, and a silkworm extract obtained by extraction, which includes the peptide cecropin, amino acids and a vitamin mixture, and a non-ionic, cationic or anionic hydrogel or a mixture of hydrogels, and one or more phospholipids, and water.

7. The method according to claim 1, wherein a peptide of the formula Lip-X-His-Phe-Arg-Y is employed as peptide, wherein Lip is thioctic acid or a derivative thereof, X is Glu, OH or $NH_2$, Y is Trp-Gly-OH, Trp-Gly-$NH_2$, Trp-OH or Trp-$NH_2$, and Phe is homo-Phe or P-fluoro-Phe.

8. The method according to claim 1, wherein a hydrolyzed *Citrus aurantinum* extract with a share of 0.5-2 wt.-% is employed in the secondary product.

9. The method according to claim 1, wherein the skin is subjected to a cleansing treatment with a skin peel immediately prior to applying the preproduct.

10. The method according to claim 1, wherein the oil of green coffee beans is encapsulated in liposomes, and that an amount of from 0.05 to 0.5 wt.-% is employed.

11. A set for cosmetic body modelling, wherein the set comprises:
a preproduct comprising active ingredients comprising 0.5-3 wt.-% caffeine, 0.1-2.5 wt.-% of an algae extract of *Gelidium* s.p., 0.05-2 wt.-% of an encapsulated pineapple fruit extract, 0.3-2.5 wt.-% of a radical scavenger, 0.005-0.1 wt.-% copper gluconate, 0.05-0.5 wt.-% of a silylpropionic acid, and 0.1-1 wt.-% of a stimulant for melanin synthesis, comprising sorbitol and Arg-HCl, Orn-HCl and Tyr,
wherein all wt.-% are based on the overall weight of the preproduct, with the proviso that the quoted amounts are balanced with water and optionally further adjuvants and additives to make 100 wt.-%;
a main product comprising the active ingredients in the amounts, except for the radical scavenger, of the preproduct and further comprising 5 to 40 wt-% of a mixture of UVA and UVB filters at a weight ratio of 30:70 to 70:30, and 0.01-3.0 wt.-% of an encapsulated oil of green coffee beans, relative to the overall weight of the main product, the share of radical scavenger being 30-60% lower than that in the preproduct, relative to the weight of radical scavenger in the preproduct, with the proviso that the quoted amounts are balanced with water and optionally further adjuvants and additives to make 100 wt.-%; and
a secondary product comprising the active ingredients in the amounts, except for the silylpropionic acid, of the preproduct, the share of silylpropionic acid being 2 to 10 times the share in the preproduct, ranging from 0.5 to 2.5 wt.-%, relative to the overall weight of the secondary product, with the proviso that the quoted amounts are balanced with water and optionally further adjuvants and additives to make 100 wt.-%.

12. The method according to claim 1, wherein a tan intensity of a subject four weeks after a final application of said secondary product is at least 80% of an initial tan intensity of said subject immediately after said final application.

13. A set for cosmetic body modelling, wherein the set consisting of:
a preproduct comprising active ingredients comprising 0.5-3 wt.-% caffeine, 0.1-2.5 wt.-% of an algae extract of *Gelidium* s.p., 0.05-2 wt.-% of an encapsulated pineapple fruit extract, 0.3-2.5 wt.-% of a radical scavenger, 0.005- 0.1 wt.-% copper gluconate, 0.05-0.5 wt.-% of a silylpropionic acid, and 0.1-1 wt.-% of a stimulant for melanin synthesis, comprising sorbitol and Arg-HCl, Orn-HCl and Tyr, wherein all wt.-% are based on the overall weight of the preproduct, with the proviso that the quoted amounts are balanced with water and optionally further adjuvants and additives to make 100 wt.-%;
a main product comprising the active ingredients in the amounts, except for the radical scavenger, of the preproduct and further comprising 5 to 40 wt-% of a mixture of UVA and UVB filters at a weight ratio of 30:70 to 70:30, and 0.01-3.0 wt.-% of an encapsulated oil of green coffee beans, relative to the overall weight of the main product, the share of radical scavenger being 30-60% lower than that in the preproduct, relative to the weight of radical scavenger in the preproduct, with the proviso that the quoted amounts are balanced with water and optionally further adjuvants and additives to make 100 wt.-%; and
a secondary product comprising the active ingredients in the amounts, except for the silylpropionic acid, of the preproduct, the share of silylpropionic acid being 2 to 10 times the share in the preproduct, ranging from 0.5 to 2.5 wt.-%, relative to the overall weight of the secondary product, with the proviso that the quoted amounts are balanced with water and optionally further adjuvants and additives to make 100 wt.-%.

* * * * *